United States Patent [19]

Chen

[11] Patent Number: 5,221,692
[45] Date of Patent: Jun. 22, 1993

[54] ETHER LINKED AND RELATIVELY NONPUNGENT ANALOGUES OF N-NONANOYL VANILLYLAMIDE

[75] Inventor: Ing-Jun Chen, Kao-Hsiung, Taiwan

[73] Assignee: National Science Council, Taipei, Taiwan

[21] Appl. No.: 748,815

[22] Filed: Aug. 22, 1991

[51] Int. Cl.$^5$ .................. A61K 31/16; C07C 103/133
[52] U.S. Cl. .................................... 514/625; 546/233; 546/234; 554/63; 554/65
[58] Field of Search ................. 514/317, 279, 625; 546/233, 234; 554/63, 65

[56] References Cited

U.S. PATENT DOCUMENTS

| | | | |
|---|---|---|---|
| 4,599,342 | 7/1986 | LaHann | 514/282 |
| 5,045,565 | 9/1991 | Gardner et al. | 514/487 |

*Primary Examiner*—C. Warren Ivy
*Assistant Examiner*—James H. Turnipseed
*Attorney, Agent, or Firm*—Bacon & Thomas

[57] ABSTRACT

The present invention provides a series of ether linked analogues of N-nonanoyl vanillylamide. They are found pharmaceutically effective in antinociceptive treatment and relatively nonpungent.

6 Claims, No Drawings

ETHER LINKED AND RELATIVELY NONPUNGENT ANALOGUES OF N-NONANOYL VANILLYLAMIDE

TECHNICAL FIELD OF THE INVENTION

The present invention relates to new and usefuls ether linked analogues of N-nonanoyl vanillylamide.

BACKGROUND OF THE INVENTION

Capsaicin (trans-8-methyl-N-vanillyl-6-nonenamide; CAP), a pungent principle of red pepper, having the formula

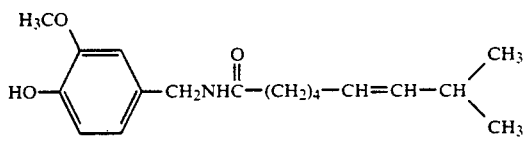

has a variety of pharmacological actions on cardiovascular and respiratory system, and on nervous system. Topical application of CAP to the skin evoked pain and may be followed by a period of desensitization to noxious chemical, thermal and mechanical stimuli. However, the initial activation of C-fibre nociceptors to produce a burning pain sensation and the concomitant hypothermia limited its use, although some clinical trials in treatment of postherpetic neuralgia have been carried out recently.

A number of analogues of CAP including vanillylacylamides, homovanillyl acylamides, carbamate derivatives, sulfonamide derivatives, urea derivatives, aralkylamides and thioamides, aralkyl aralkanamides, phenylacetamides and phenylacetic acid esters have been synthesized, and some of them have also been evaluated for their pungent potencies, desensitizing effects and antinociceptive activities. However, as yet none have been found to surpass the effectiveness of CAP. The most potent of the analogues synthesized thus far is N-nonanoyl vanillylamide (nonivamide; NVA), found to have a pharmacological profile similar to that of CAP and has been used as a substitute for CAP in neurophysiological and neuropharmacological studies. It has the formula as follows and is available today both commercially and in reagent-grade purity:

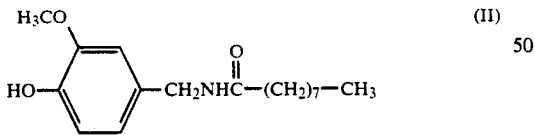

Besides, a novel analogue of CAP, olvanil (N-vanillyl-9-octadecenamide; NE-19550), has been claimed to be a new class of anti-inflammatory analgesic agent with high oral $ED_{50}$ of 170 mg/kg.

Most of the analogues of CAP have been derived from modifications of either the acylamide linkage or the alkyl chain. Some observations have pointed to the central role of the phenolic hydroxyl group in the bioactivity of CAP.

Szolcsanyl and Jansco-Gabor in their articles, *Arzneium.-Forsch./Drug Res.* 25, 1877 (1975) and *Arzneim.-Forsch./Drug Res.* 26, 33 (1976), report that 3-methoxy, 4-hydroxy phenyl ring is essential to the pungency of the capsaicin molecule, wherein an ether linked analogues of CAP is synthesized by replacing the free phenolic OH group with $OCH_3$ group. However, they also report that this replacement can lead to a marked decrease, or a complete loss of other bioactivities such as antinociceptive and hypothermic activities as well.

As a result of an extensive investigations to develop a more potent, less acute and cardiac toxicity agent than that of capsaicin or of its analogues, a novel series of ether linked analogues of N-nonanoyl vanillylamide have been newly synthesized in the present invention.

Accordingly, one object of the present invention is to provide new and useful ether linked analogues of N-nonanoyl vanillylamide and pharmaceutically acceptable salts thereof.

Another object of the present invention is to provide a process for preparing the ether linked analogues of N-nonanoyl vanillylamide and pharmaceutically acceptable salts thereof.

A further object of the present invention is to provide a pharmaceutical composition containing, as an active ingredient, the ether linked analogues of N-nonanoyl vanillylamide or a pharmaceutically acceptable salt thereof.

Still another object of the present invention is to provide a method for the antinociceptive treatment comprising administrating to a mammal in need of said treatment an effective amount of the ether linked analogues of N-nonanoyl vanillylamide or a pharmaceutically acceptable salt thereof.

SUMMARY OF THE INVENTION

The present invention provides novel ether linked analogues of N-nonanoyl vanillylamide having the formula:

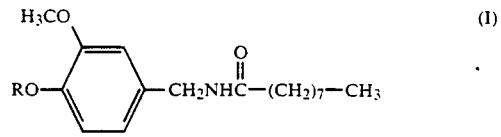

wherein:
R is $C_2$–$C_4$ alkoxy, $C_2$–$C_4$ carboxyl, $C_1$–$C_4$ alkyl(pyridyl), $C_1$–$C_4$ alkyl(piperidyl), or

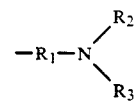

wherein
$R_1$ is $C_1$–$C_4$ alkyl; $R_2$ is hydrogen, $C_1$–$C_4$ alkyl; $R_3$ is hydrogen, $C_1$–$C_4$ alkyl; or $R_2$ and $R_3$ together represent $C_2$–$C_6$ alkylene or

and pharmaceutically acceptable salts thereof.

The compounds of formula (I) and the salts thereof have a potent antinociceptive activity without producing overt pungent and irritating effects, and they are, therefore, more suitable for being used as a pharmaceutical than conventional pungent capsaicin derivatives.

DETAILED DESCRIPTION OF THE PREFERRED EMBODIMENTS

The pharmacologically allowable salts include inorganic acid salts such as hydrochlorides, sulfates, hydrobromides, perchlorates and nitrates; and organic acid salts such as oxalates, maleates, funarates, succonates and methanesulfonates.

Preferred compounds within the scope of formula (I) are R is $C_2-C_3$ carboxyl, and

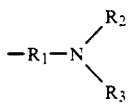

wherein $R_1$ is ethyl; $R_2$ is methyl or ethyl; and $R_3$ is methyl or ethyl. Among them N-(4-o-acetic acid-3-methoxybenzyl)-nonamide, i.e. R is $C_2$ carboxyl, and its alkali metal salts are most preferable.

The ether linked analogues of N-nonanoyl vanillylamide of formula (I) can be prepared by introducing side chains to the phenolic hydroxyl group in position 4 on the aromatic ring of N-nonanoyl vanillylamide having the formula (II).

A process suitable for preparing the compounds of formula (I) comprises reacting N-nonanoyl vanillylamide of formula (II) which a compound of formula Y-R in a basic medium, wherein Y is halogen, preferably Y is chloride, R has the same meaning defined above.

The compounds of formula (I) and the salts thereof are found excellent in antinociceptive activity without producing overt pungent and irritating effects. The high antinociceptive potencies with low acute toxicities thereof allow them to be the potential candidates as antinociceptive agents.

In the following examples the compounds of formula (I) are synthesized and identified, and the pharmocology thereof are also examined. These examples are only meant to illustrate the present invention not for limiting the scope thereof.

EXAMPLE

The purpose of this example is to synthesize intravenously activated, nonpungent antinociceptive analogues of CAP that show less acute and cardiac toxicity than that of CAP or of its analogue, NAV. To this end a series of analogues of NAV were prepared by introducing side chains to the phenolic hydroxl group in position 4 on the aromatic ring (Scheme I).

Scheme 1

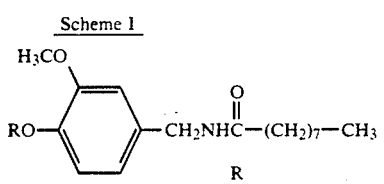

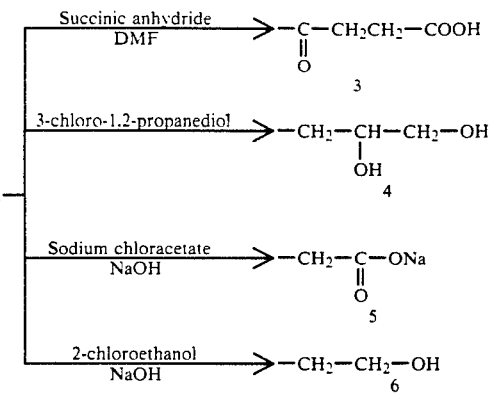

Ether analogues 4, 5 and 6 were obtained by reacting NVA with 3-chloro-1,2-propanediol, sodium chloroacetate, and 2-chloroethanol, respectively, in basic medium. The ester 3 was synthesized by treating NVA with succinc anhydride in DMF.

Synthesis

N-(4-o-succinicacid-3-methoxybenzyl)-nonamide(N-nonanoyl vanillylamide-4-succinyl ester, 3)

A solution in DMF (0.1 ml) of NVA (2.00 g, 6.82 mmol) and succinic anhydride (0.8 gm, 8.0 mmol) in a 3-necked flask, was heated at 100° C. for on hour, then diluted with ethyl acetate (10 mL) and extracted with 20 mL of sodium hydroxide solution (0.5%) in a separatory funnel. The lower layer was acidified with conc. HCl to pH 4.0 and extracted with ethyl acetate. The organic layer was then separated and evaporated to dryness under reduced pressure. The residue crystallized from benzene to give 3 (1.3 g, 48%) as colorless needless: mp 104°-106° C. UV $\lambda_{Max}^{MeOH}$ nm (log ε): 275 (3.49), 279 (3.48). NMR (CDCl$_3$) δ: 0.87 (t, 3H, CH$_3$), 1.25-2.25 (m, 14H, CH$_2$×7), 2.77-2.90 (m 4H, Ch$_2$×2), 3.75 (s, 3H, OCH$_3$), 4.34 (d, 2H, Ar—CH$_2$), 6.32 (s, 1H, NH), 6.76-6.97 (m, 3H, Ar), 9.92 (br, s, 1H, COOH); IR (KBr); 1698, 1700 cm$^{-1}$; MS m/z 394 (M+H)$^+$. The elemental analysis is listed as follows

| 3: C$_{21}$H$_{31}$NO$_6$ | Calcd. | C: 64.10; | H: 7.94; | N: 3.56 |
|---|---|---|---|---|
| | Found | C: 63.79; | H: 7.90; | N: 3.57 |

N-(4-o-glycerol-3-methoxybenzyl)-nonamide (N-nonanoyl vanillylamide-4-glyceryl ether, 4)

A mixture of NVA (2.64 g, 9.0 mmol), 3-chloro-1,2-propanediol (1 ml) and 30% NaOH (1.2 mL), was heated at reflux for one hour. After cooling, conc. HCl was added until pH 4.0, the inorganic salt filtered off and the filtrate diluted with methanol. The solid separated was recrystallized from benzene to afford 4 (2.1 g, 64%) as colorless needles; mp 133° C., UV $\lambda_{Max}^{MeOH}$ nm (log ε): 227.3 (4.57), 275.6 (3.90), NMR (CDCl$_3$) δ: 0.86 (m, 3H, CH$_3$), 1.25-2.22 (m, 14H, CH$_3$), 1.25-2.22 (m, 14H, CH$_2$x7), 2.37 (t, 1H, CHOH), 3.05 (s, 1H, CH$_2$OH), 3.79 (d, 2H, CH$_2$OH), 3.84 (s, 3H, OCH$_3$), 4.05 (d, 2H, OCH$_2$CH), 4.15 (t, 1H, OCH$_2$CH), 4.37 (d, 2H, Ar-CH$_2$), 5.8 (s, 1H, NH), 6.80-6.87 (m, 3H, Ar); IR (KBr): 3280, 1640, 1020, 1150 cm$^{-1}$; MS m/z 367 (M)$^+$.

| 4: $C_{20}H_{33}NO_5$ | Calcd. | C: 65.39; | H: 8.99; | N: 3.81 |
|---|---|---|---|---|
| | Found | C: 65.33; | H: 8.95; | N: 3.85 |

N-(4-o-acetic acid sodium-3-methoxybenzyl-nonamide(sodium N-nonanoyl vanillylamide-4-o-acetate, 5)

Sodium chloroacetate (0.80 g, 9.76 mmol) was added to a solution of NVA (2.00 g, 6.82 mmol) in 30 ml of a 0.4 M NaOH. The mixture was heated at reflux for two hours, concentrated unreduced pressure and residue was crystallized from absolute ethanol to afford 5 (1.2 g, 44%) as colorless needles: mp 196°–199° C. UV $\lambda^{MeOH}$ nm (log $\epsilon$): 231 (4.25), 280 (3.92), NMR (DMSO-$d_6$) $\delta$: 0.79–0.96 (t, 3H, $CH_3$), 1.24–2.17 (m, 14H, $CH_2 \times 7$), 3.74 (s, 3H, $OCH_3$), 4.07 (s, 2H, $OCH_2O$), 4.13–4.19 (d, 2H, Ar—$CH_2$), 6.72–6.82 (d, 3H, ar), 8.21 (s, 1H, NH), IR (KBr): 1520, 1580, 1600, 1640, 3300 cm$^{-1}$; MS m/z 396 $(M+H)^+$.

| 5: $C_{19}H_{28}NO_5Na \cdot 2H_2O$ | | | | |
|---|---|---|---|---|
| Calcd. | C: 55.75; | H: 7.82; | N: 3.42; | O: 27.38 |
| Found | C: 55.82; | H: 7.79; | N: 3.45; | O: 27.34 |

N-(4-o-glycol-3-methoxybenzyl)-nonamide (N-nonanoyl vanillylamide-4-glycol ether, 6)

In a 3-necked flash a mixture of NVA (2.00 g, 6.82 mmol), 0.46 ml 2-chloroethanol and 1 ml of 30% sodium hydroxide was heated at 100° C. for one hour. Following the procedure reported for 4 a product was isolated which crystallized from benzene to give 1.4 g (61%) of 6 as colorless needles: mp 116°–117° C. UV $\lambda_{Max}^{MeOH}$ nm (log $\epsilon$); 230 (4.05), 279 (1.83), NMR (CDCl$_3$) $\delta$:0.84 (m, 3H, $CH_3$), 1.23–2.18 (m, 14H, $CH_2 \times 7$), 2.27 (s, 1H, OH), 3.82 (s, 3H, $OCH_3$), 3.89 (t, 2H, $CH_2OH$), 4.08 (t, 2H, $OCH_2$), 4.33 (d, 2H, Ar—$CH_2$), 5.77 (s, 1H, NH), 6.79 (m, 3H, Ar); IR (KBr): 3280 cm$^{-1}$; MS m/z 337 $(M+)^+$.

| 6: $C_{19}H_{31}NO_4$ | Calcd. | C: 67.66; | H: 9.20; | N: 4.15 |
|---|---|---|---|---|
| | Found | C: 67.59; | H: 9.18; | N: 4.20 |

All melting points were determined in a Yanagimoto MP-3 micromelting point apparatus and are uncorrected. The putative structures of all compounds were supported by data derived from infrared (IR) and nuclear magnetic resonance (NMR) spectra. IR spectra were determined with the Hitachi Model 260-30 recording spectrometer, and NMR spectra were recorded on a Varian T-200 spectrometer. Mass spectra were determined on a Jeol JMS-HX 110 mass spectrometer. Compound NVA, sodium chloroacetate, 3-chloro-1,2-propanediol, and 2-chloroethanol and were all obtained from Tokyo Chemical Industry Co. (T.C.I). Succinic anhydride and sodium hydroxide were products of E. Merck, capsaicin (98% pure) and indomethacin were products of Sigma Co. All other reagent used in this study were E.P. grade products of E. Merck.

PHARMACOLOGY

Evaluation of the potency of pungency

The wiping test was performed as described by Szolcsanyi and Jansco-Gabor, Arzneim.-Forsch./Drug Res. 25, 1877 (1975). Briefly, solutions of CAP and its analogues were prepared as described above in successive tenfold dilutions. Each dilution was dropped into the right eye (vehicle being administered to the left eye as negative control) of male Wistar rats weighing 180–250 g, and the total number of protective movements (scratching, wiping of the eye with the foreleg) was counted for 30 min. Each concentration was applied to a total of 6 rats, and a dose-response curve were obtained form the mean value of each group. MPPs (the concentrations having a moderate pain-producing potency) were calculated from the dose-response curve and those concentrations inducing equal reactions of 32 scratchings (the median response induced by CAP) were recorded. On the basis of the MPP values thus obtained, RPP (relative pain-producing potency) values were determined with respect to the pain-producing potency of CAP, which was taken as 1000. The results are shown in Table 1.

TABLE 1

The relative pungent potencies of capsaicin and its analogues as measured by the wiping test[a].

| Compound | MPP[b] (mg/ml) | RPP[c] |
|---|---|---|
| Capsaicin | 0.09 | 1000 |
| NVA | 0.22d | 409 |
| 3 | 0.27[d),e] | 333 |
| 4 | — | — |
| 5 | — | — |
| 6 | — | — |

[a]Methods are described by Szolcsanyi & Jansco-Gabor.
[b]MPP = Moderate pain-producing potency.
[c]RPP = Relative pain-producing potency.
[d]Significantly different as compared to capsaicin, $p < 0.05$, n = 8 (student's t-test).
[e]Nonsignificantly different as compared to compound CAP, $p > 0.05$, n = 8 (student's t-test).
—: Relatively nonpungent as compared to capsaicin (no. of wiping movements are far less than the median scratchings induced by capsaicin throughout the concentrations tested.

The results of Table 1 indicate that all but one of the analogues are nonpungent in comparison to NVA and CAP. The pungency of 3 is nearly equivalent to that of NVA and CAP, while ether linked analogue 4–6 are relatively nonpungent. This suggests a metabolic cleavage of the ester linkage of analogue 3 to revert to the parent compound, NVA.

Evaluation of antinociceptive effects Following the method described by Koster et al., Fed. proc. 18, 412 (1959), antinociceptive tests were carried out in male mice after intraperitoneal administration of NVA and its analogues. Briefly, four groups of eight male mice (ddk strain) weighing 18–22 g were brought to the laboratory on the day prior to study, and housed overnight with free access to food and water. Solutions of NVA and its analogues, as well as indomethacin were made up to 10% ethanol, 10% between 80% saline, and then diluted with saline to the required concentrations. The test solution was administered by intraperitoneal injection with single dose of 0.2 mL (vehicle administered as control). 20 min after injection, 0.2 mL of 0.7% acetic acid was injected intraperitoneally to induce writhing. Following injection, the mice were placed in separate clear glass cages and the number of writhes was counted for 18 consecutive 5 min periods beginning 5 min after acetic acid injection, a writhe being defined as a sequence of arching of the back, followed by pelvic rotation and hind limb extension. The results are shown in Table 2.

TABLE 2

Antinociceptive effects of capsaicin analogues on acetic acid-induced writhing in mice[a].

| Compound | $ED_{50}$ (95% C.L.)[b] (mg/kg) | Potency ratio |
|---|---|---|
| Indomethacin | 1.10 (2.57–0.47) | 1.00 |
| NVA | 0.08 (0.42–0.02) | 13.75 |
| CAP | 0.07 (0.33–0.02) | 15.71 |
| 3 | 0.06 (0.30–0.01) | 18.33 |
| 4 | 0.09 (0.38–0.02) | 12.22 |
| 5 | 0.04 (0.13–0.01) | 27.50 |
| 6 | 0.14 (0.43–0.04) | 7.86 |
| 7 | 0.15 (0.48–0.04) | 7.33 |

[a]Writhes were counted for 30 min after injection of acetic acid (i.p.).
[b]$ED_{50}$ and 95% confidence limits were calculated by the Litchfield and Wilcoxon method.

All mice treated with these compounds showed a doserelated decrease in writhing counts induced by acetic acid. Indomethacin was used as reference drug. Writhing was most pronounced for thirty minutes following the administration of acetic acid, gradually subsiding after having reached a peak in the first 10–15 minutes. The $ED_{50}$ values (Table 2) clearly show analogue 5 to be the most potent in its antinociceptive effect.

In conclusion, 4-phenolic ether-substituted analogues of NVA, i.e., 4–6, still retain marked antinociceptive and hypotensive effects without demonstrating overt irritant effects.

What is claimed is:

1. An ether linked analogue of N-nonanoyl vanillylamide having the formula:

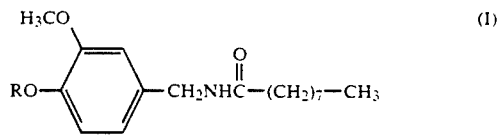

wherein
R is $C_2$–$C_4$ carboxyl, —$CH_2CH(OH)CH_2OH$ or —$CH_2CH_2OH$;
and pharmaceutically acceptable salt thereof.

2. A pharmaceutical composition for antinociceptive treatment of a mammal comprising a therapeutically effective amount of an ether linked analogue of N-nonanoyl vanillylamide of the formula (I) as defined in claim 1 or a pharmaceutically acceptable salt thereof as active ingredient, in combination with a pharmaceutically acceptable carrier or diluent.

3. A method for antinociceptive treatment of a mammal comprising administering to a mammal in need of such treatment a therapeutically effective amount of an ether linked analogue of N-nonanoyl vanillylamide of the formula (I) as defined in claim 1 or a pharmaceutically acceptable salt thereof.

4. An ether linked analogue according to claim 1, wherein R is —$CH_2COOH$.

5. A pharmaceutical composition according to claim 2, wherein R is —$CH_2COOH$.

6. A method according to claim 3, wherein R is —$CH_2COOH$.

* * * * *